US00PP20600P2

(12) United States Plant Patent
Arts

(10) Patent No.: US PP20,600 P2
(45) Date of Patent: Dec. 22, 2009

(54) ***KALANCHOE* PLANT NAMED 'ABALPHA'**

(50) Latin Name: *Kalanchoe blossfeldiana*
Varietal Denomination: Abalpha

(75) Inventor: Niels Arts, Aalsmeer (NL)

(73) Assignee: AB Breeding, De Kwakel (NL)

( * ) Notice: Subject to any disclaimer, the term of this patent is extended or adjusted under 35 U.S.C. 154(b) by 0 days.

(21) Appl. No.: 12/228,281

(22) Filed: Aug. 11, 2008

(51) Int. Cl.
*A01H 5/00* (2006.01)

(52) U.S. Cl. ..... Plt./341
(58) Field of Classification Search ..... Plt./341
See application file for complete search history.

*Primary Examiner*—June Hwu
(74) *Attorney, Agent, or Firm*—C. A. Whealy

(57) ABSTRACT

A new and distinct cultivar of *Kalanchoe* plant named 'Abalpha', characterized by its upright, outwardly spreading and uniform plant habit; vigorous growth habit; freely branching habit; dark green-colored leaves; early, uniform and freely flowering habit; dark red-colored flowers; and good postproduction longevity.

1 Drawing Sheet

Botanical designation: *Kalanchoe blossfeldiana.*
Cultivar denomination: 'Abalpha'.

BACKGROUND OF THE INVENTION

The present invention relates to a new and distinct cultivar of *Kalanchoe*, botanically known as *Kalanchoe blossfeldiana*, and hereinafter referred to by the name 'Abalpha'.

The new *Kalanchoe* plant is a product of a planned breeding program conducted by the Inventor in De Kwakel and Middelburg, The Netherlands. The objective of the breeding program is to create new freely branching and compact *Kalanchoe* cultivars with attractive foliage and flower coloration.

The new *Kalanchoe* plant originated from a cross-pollination made by the Inventor in De Kwakel, The Netherlands in October, 2005, of a proprietary selection of *Kalanchoe blossfeldiana* identified as code number 204105-03, not patented, as the female, or seed parent with a proprietary selection of *Kalanchoe blossfeldiana* identified as code number 203009, not patented, as the male, or pollen, parent. The new *Kalanchoe* was discovered and selected by the Inventor as a single flowering plant from within the progeny of the stated cross-pollination in a controlled greenhouse environment in Middelburg, The Netherlands in August, 2006.

Asexual reproduction of the new *Kalanchoe* plant by vegetative terminal cuttings in a controlled greenhouse environment in De Kwakel, The Netherlands since August, 2006, has shown that the unique features of this new *Kalanchoe* plant are stable and reproduced true to type in successive generations.

SUMMARY OF THE INVENTION

Plants of the new *Kalanchoe* have not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Abalpha'. These characteristics in combination distinguish 'Abalpha' as a new and distinct cultivar of *Kalanchoe:*

1. Upright, outwardly spreading and uniform plant habit.
2. Vigorous growth habit.
3. Freely branching habit.
4. Dark green-colored leaves.
5. Early, uniform and freely flowering habit.
6. Dark red-colored flowers.
7. Good postproduction longevity.

Plants of the new *Kalanchoe* can be compared to plants of the female parent selection. Plants of the new *Kalanchoe* differ primarily from plants of the female parent selection in flower color as plants of the new *Kalanchoe* have darker red-colored flowers than plants of the female parent selection.

Plants of the new *Kalanchoe* can also be compared to plants of the male parent selection. Plants of the new *Kalanchoe* differ from plants of the male parent selection primarily in flower color as plants of the male parent selection have red purple-colored flowers. In addition, plants of the new *Kalanchoe* have larger leaves than plants of the male parent selection.

Plants of the new *Kalanchoe* can be compared to plants of *Kalanchoe blossfeldiana* 'Illoide', not patented. In side-by-side comparisons conducted in De Kwakel, The Netherlands, plants of the new *Kalanchoe* differed from plants of 'Illoide' in the following characteristics:

1. Plants of the new *Kalanchoe* were larger than plants of 'Illoide'.
2. Plants of the new *Kalanchoe* had larger flowers than plants of 'Illoide'.
3. Plants of the new *Kalanchoe* had darker red-colored flowers than 'Illoide'.
4. Flowers of plants of the new *Kalanchoe* had ovate-shaped petals whereas plants of 'Illoide' had elliptic-shaped petals.

BRIEF DESCRIPTION OF THE PHOTOGRAPH

The accompanying colored photograph illustrates the overall appearance of the new *Kalanchoe*, showing the colors as true as it is reasonably possible to obtain in colored reproductions of this type. Colors in the photograph may differ slightly from the color values cited in the detailed botanical description which accurately describe the colors of the new *Kalanchoe* plant. The photograph comprises a side perspective view of a typical flowering plant of 'Abalpha' grown in a container.

DETAILED BOTANICAL DESCRIPTION

The aforementioned photograph and following observations, measurements and values describe plants grown in De Kwakel, The Netherlands in a glass-covered greenhouse during the spring and under conditions which closely approximate commercial *Kalanchoe* production. During the production of the plants, day and night temperatures averaged 20° C. and light levels averaged 500 watts per square meter. Unrooted cuttings were directly stuck in containers and received long day/short night conditions (more than 14 hours of light) for about four weeks; plants then received photoinductive short day/long night conditions (minimum 14 hours darkness) until flowering. Plants were four months from planting when the photograph and the description were taken. In the detailed description, color references are made to The Royal Horticultural Society Colour Chart, 2001 Edition, except where general terms of ordinary dictionary significance are used.

Botanical classification: *Kalanchoe blossfeldiana* 'Abalpha'.

Parentage:

*Female, or seed, parent.*—Proprietary selection of *Kalanchoe blossfeldiana* identified as code number 204105-03, not patented.

*Male or pollen parent.*—Proprietary selection of *Kalanchoe blossfeldiana* identified as code number 203009, not patented.

Propagation:

*Type.*—By vegetative terminal cuttings.

*Time to initiate roots, summer.*—About ten days at temperatures of 20° C.

*Time to initiate roots, winter.*—About two weeks at temperatures of 20° C.

*Time to produce a rooted young plant, summer.*—About three weeks at temperatures of 20° C.

*Time to produce a rooted young plant, winter.*—About 25 days at temperatures of 20° C.

*Root description.*—Fine, fibrous; brown in color.

*Rooting habit.*—Freely branching; moderately dense.

Plant description:

*Plant habit.*—Upright, outwardly spreading and uniform plant habit; rounded crown.

*Growth habit.*—Vigorous; rapid growth rate.

*Plant height.*—About 23 cm.

*Plant diameter.*—About 26 cm.

*Branching habit.*—Freely branching habit; about eight lateral branches develop per plant. Pinching (removal of the terminal apex) is typically not required but will enhance lateral branch development.

Lateral branch description:

*Length.*—About 18 cm to 20 cm.

*Diameter.*—About 6 mm.

*Internode length.*—About 2 cm to 3 cm.

*Aspect.*—Erect.

*Strength.*—Strong.

*Texture.*—Smooth, glabrous.

*Color.*—Close to 146B.

Foliage description:

*Arrangement.*—Opposite, simple; generally symmetrical.

*Length.*—About 9 cm to 10 cm.

*Width.*—About 6 cm to 7 cm.

*Shape.*—Ovate.

*Apex.*—Obtuse.

*Base.*—Cuneate.

*Margin.*—Crenate.

*Texture, upper and lower surfaces.*—Smooth, glabrous.

*Venation pattern.*—Pinnate.

*Color.*—Developing leaves, upper surface: Between 146B and 137C. Developing leaves, lower surface: Close to 146B. Fully expanded leaves, upper surface: Close to 147A; venation, close to 147B. Fully expanded leaves, lower surface: Close to 147B; venation, close to 147B.

*Petiole.*—Length: About 1 cm. Diameter: About 4 mm. Texture, upper and lower surfaces: Smooth, glabrous. Color, upper and lower surfaces: Close to 147B.

Flower description:

*Flower arrangement and habit.*—Single flowers arranged in compound axillary cymes. Uniform and freely flowering habit with usually about 60 to 80 flowers developing per lateral stem.

*Natural flowering season.*—Plants of the new *Kalanchoe* flower naturally in the fall. Flower initiation and development can also be induced under artificial short day/long conditions (at least 14 hours of darkness) year-round in a greenhouse environment.

*Time to flower.*—Under short day/long night photoinductive conditions, about eight weeks are required. Actual time to flower is dependent upon temperature and light intensity.

*Post-production longevity.*—Excellent post-production longevity; plants maintain good foliage and flower substance for about five weeks under interior environmental conditions; flowers persistent.

*Fragrance.*—Not detected.

*Flower diameter.*—About 1.5 cm.

*Flower length* (*height*).—About 1.8 cm.

*Flower bud.*—Shape: Elliptical. Length: About 8 mm. Diameter: About 2 mm. Color: Close to 179B to 179C.

*Petals.*—Arrangement: About four in a single whorl fused at the base. Length: About 6 mm. Width: About 5 mm. Aspect: Upright to eventually perpendicular to the pedicel. Shape: Ovate. Apex: Cuspidate. Margin: Entire. Texture, upper and lower surfaces: Smooth, glabrous. Color: When opening, upper surface: Close to 45B. When opening, lower surface: Between 179D and 180C. Fully opened, upper surface: Close to 53B; color becoming closer to 60A with development. Fully opened, lower surface: Close to 51B to 51D.

*Sepals.*—Appearance: Four fused at the base. Length: About 6 mm. Width: About 1.5 mm. Shape: Lanceolate. Apex: Acute. Base: Obtuse. Margin: Entire. Texture, upper and lower surfaces: Smooth; glabrous. Color, immature, upper and lower surfaces: Close to 144A. Color, mature, upper and lower surfaces: Close to 144A.

*Peduncles.*—Length: About 3 cm to 5 cm. Diameter: About 4 mm. Aspect: Mostly erect. Strength: Strong. Texture: Smooth, glabrous. Color: Close to 146B.

*Pedicels.*—Length: About 3 mm to 4 mm. Diameter: About 1 mm. Aspect: Erect to about 90° from vertical. Strength: Strong. Texture: Smooth, glabrous. Color: Close to 146B.

*Reproductive organs.*—Androecium: Stamen number: About eight per flower. Anther shape: Oval. Anther length: About 1 mm. Anther color: Close to 28C. Amount of pollen: Abundant. Pollen color: Close to 6C. Gynoecium: Pistil number: About four per flower. Pistil length: About 4 mm. Style length: About 3 mm. Style color: Close to 145C. Stigma shape: Round. Stigma color: Close to 145C. Ovary color: Close to 143C.

*Seeds.*—Quantity per flower: Abundant. Length: Less than 1 mm. Diameter: Less than 1 mm. Color: Close to 200A.

Temperature tolerance: Plants of the new *Kalanchoe* have been observed to tolerate temperatures from about 17° C. to about 40° C.

Pathogen/pest resistance: Plants of the new *Kalanchoe* have not been observed to be resistant to pests and pathogens common to *Kalanchoes.*

It is claimed:

1. A new and distinct *Kalanchoe* plant named 'Abalpha' as illustrated and described.

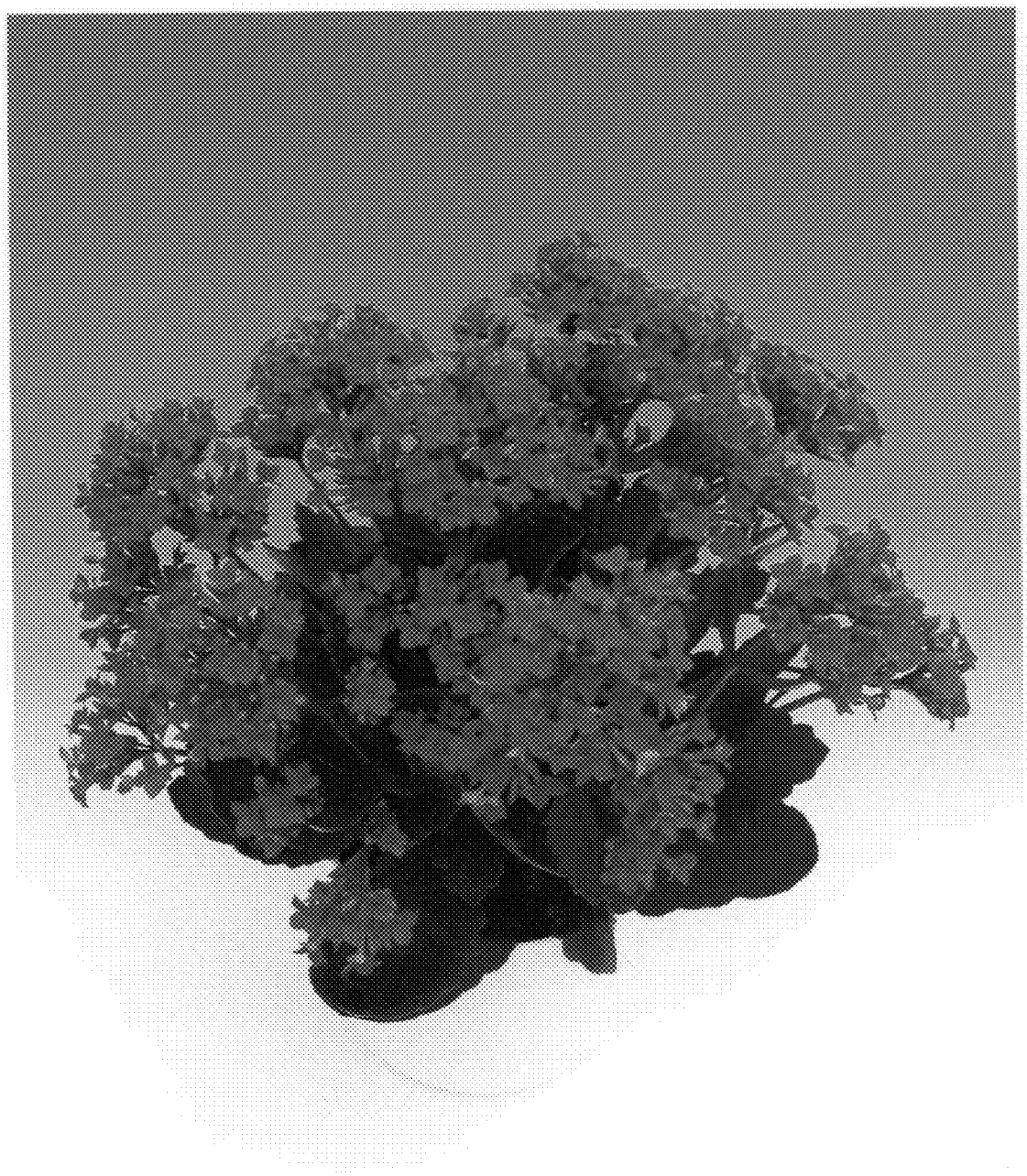

* * * * *